US005173479A

United States Patent [19]

Tajima et al.

[11] Patent Number: 5,173,479

[45] Date of Patent: Dec. 22, 1992

[54] MODIFIED BASIL ESSENTIAL OIL AND PROCESS FOR THE PRODUCTION THEREOF

[75] Inventors: Katsuhiko Tajima; Yoshihiro Hasegawa, both of Chiba, Japan

[73] Assignee: KAO Corporation, Tokyo, Japan

[21] Appl. No.: 765,940

[22] Filed: Sep. 26, 1991

[30] Foreign Application Priority Data

Oct. 19, 1990 [JP] Japan .................................. 2-281330

[51] Int. Cl.[5] ................................................ A61K 7/46

[52] U.S. Cl. ........................................................ 512/5

[58] Field of Search ........................................ 512/1, 5

[56] References Cited

FOREIGN PATENT DOCUMENTS 679774 4/1930 France .................................... 512/1

OTHER PUBLICATIONS

World Patents Index Latest, Section Ch, Week 8940, Derwent Publications, Ltd., London, GB, Class D, AN 89-291485.

World Patents Index Latest, Section Ch, Week 8251, Derwent Publ. Ltd., London, GB, Class D, AN 82-11357J.

World Patents Index Latest, Section Ch, Week 8412, Derwent Publ. Ltd., London, GB, Class D, AN 84-073186.

Indian Perfumer 31 (2), 1987, pp. 137-145, "Essential Oil of Sacred Basil (Ocimum Sanctum)," by M. L. Maheshwari et al.

"Hawley's Chemical Dictionary" 1035 (11th ed. 1987).

Maheshwari et al., Chem. Abst., vol. 109, #01338g (1988).

Pareek et al., Chem. Abst., vol. 99, #110529f (1983).

Fleisher, Chem. Abst., vol. 96, #159255r (1982).

Gulati, Chem. Abst., vol. 92, #64520b (1980).

Fenaralis, "Handbook of Flavor Ingredients", vol. 1, pp. 283-285 (1984).

Krishnamoorthy, Chem. Abst., vol. 112, #2231049 (1990).

*Primary Examiner*—James H. Reamer

*Attorney, Agent, or Firm*—Birch, Stewart, Kolasch & Birch

[57] ABSTRACT

The modified basil essential oil of the present invention comprises 87% by weight or more of sesquiterpene compounds.

The process for the production of a modified basil essential oil of the present invention comprises rectifying basil essential oil to thereby distill a fraction of a boiling point of from 82° to 92° C. under reduced pressure (2.0 to 3.0 mmHg), treating the distillate with an alkali and removing the aqueous phase to thereby give a modified basil essential oil containing 87% by weight or more of sesquiterpene compounds.

13 Claims, No Drawings

MODIFIED BASIL ESSENTIAL OIL AND PROCESS FOR THE PRODUCTION THEREOF

BACKGROUND OF THE INVENTION

1. Field of the Invention

This invention relates to a modified basil essential oil and a process for the production thereof. More particularly, it relates to a basil essential oil which has been improved in its odor or aroma so as to be effectively available as a perfume material for use in, for example, compound perfumes to elevate the content of specific components thereof. The present invention also relates for treating basil essential oil in such a manner as to elevate the content of specific components.

2. Description of the Prior Art

Natural basil essential oil widely used for compound perfumes in various cosmetics, perfumes and the like, contains estragole and linalool as the major components. It is thought that basil essential oil further contains a number of sesquiterpene hydrocarbons and oxygenated sesquiterpenes in trace amounts.

However it is very difficult to synthesize the aforesaid sesquiterpene compounds. It is known that the content of sesquiterpene compounds in basil essential oil can be elevated by steam distillation. However the distillate thus obtained usually comprises 10% by weight of sesquiterpene hydrocarbons, 0.3% by weight of oxygenated sesquiterpenes, 60 to 80% by weight of estragole, 10 to 40% by weight of linalool and 5% by weight of eugenol. Estragole exists as the major component, and substances of similar properties are contained together therein. This makes it very difficult to separate the sesquiterpene compounds at a high yield. Thus a method of efficiently separating these components on an industrial scale has not been developed.

In order to produce a compound perfume having the smell of sesquiterpene compounds accentuated, it is therefore necessary to use a large amount of basil essential oil. As a result, the content of estragole and linalool as the major components is undesirably increased, which makes it difficult to obtain a compound perfume having a desired note. Thus the range of application of basil essential oil as a perfume material is restricted.

SUMMARY OF THE INVENTION

It is an object of the present invention to provide a modified basil essential oil which has been improved in its odor or aroma so as to be effectively available as a perfume material of, for example, compound perfumes and to provide a process for the production thereof.

The present inventors have conducted extensive studies to find out that the above object can be achieved by providing a basil essential oil wherein the content of sesquiterpene compounds has been elevated above a given level, in particular, a basil essential oil which has been modified in such a manner that the content of sesquiterpene hydrocarbons having 15 carbon atoms and oxygenated sesquiterpenes is elevated each above a given level.

Accordingly, the present invention, which has been accomplished based on the above finding, provides a modified basil essential oil containing 87% by weight or more of sesquiterpene compounds.

The present invention further provides a preferable process for the production of the modified basil essential oil which comprises fractionating basil essential oil to thereby distill a fraction having a boiling point of 82° to 92° C. under reduced pressure (2.0 to 3.0 mmHg), treating this fraction with an aqueous alkali and removing the aqueous phase to thereby give the modified basil essential oil as set forth in claim 1.

The modified basil essential oil of the present invention is one improved in its odor or aroma, so as to be effectively available as a perfume material of, for example, compound perfumes, and can be relatively easily produced according to the process of the present invention.

DETAILED DESCRIPTION OF THE INVENTION

The modified basil essential oil of the present invention contains 87% by weight or more of sesquiterpene compounds. When the content of the sesquiterpene compounds is less than 87% by weight, the modified basil essential oil can barely gives characteristic odor or aroma of the sesquiterpene compounds when used as a perfume material. It is preferable that the sesquiterpene compounds substantially comprises sesquiterpene hydrocarbons having 15 carbon atoms and oxygenated sesquiterpenes; that the content of the sesquiterpene hydrocarbons in the modified basil essential oil is 85% by weight or more; and that the content of the oxygenated sesquiterpenes therein is 2% by weight or more. A modified basil essential oil, which contains from 85 to 95% by weight of the sesquiterpene hydrocarbons and from 2 to 7% by weight of the oxygenated sesquiterpenes, shows an improved odor or aroma and thus is optimal as a perfume material for producing a compound perfume having a fully accentuated odor or aroma of the sesquiterpene compounds.

The above-mentioned sesquiterpene hydrocarbons involve, for example, caryophyllene, elemene, cadinene and bisabolene, while the oxygenated sesquiterpenes refer to compounds wherein one or more oxygen atoms are attached to the above-mentioned sesquiterpene hydrocarbons. Examples thereof include bisabolol, ledol, sepathulenol, cadinol, caryophyllene oxide, nerolidol and farnesol.

It is further preferable that the content of each of estragole, linalool and eugenol in the modified basil essential oil of the present invention be 0.5% by weight or less. Although the presence of estragl, linalool and eugenol even in small amounts in the modified basil essential oil of the present invention is not preferable in order to obtain a desired odor, the scent of the sesquiterpene compounds can be sufficiently accentuated when the content of each of these components is 0.5% by weight or less.

Now a preferable example of the embodiment of the process for the production of the modified basil essential oil of the present invention having the aforementioned composition will be described.

First, the natural basil essential oil is rectified. The rectifying tower to be used in this procedure preferably has 10 or more plates. The rectification is preferably performed under reduced pressure (2.0 to 3.0 mmHg) at a temperature ranging from room temperature to 120° C. It is furthermore preferable to effect the heating as mildly as possible.

Thus the rectification is performed under the above-mentioned conditions and the fractions ranging from the first run to the fraction of a boiling point of 81° C. are removed and a fraction of a boiling point of from 82° to 92° C. is distilled.

Next, the above distillate is treated with an alkali. This treatment may be effected by adding 90 to 110 parts by weight of a 0.8 to 1.2 N aqueous solution of an alkali such as sodium hydroxide, sodium carbonate, potassium hydroxide or calcium hydroxide to 100 parts by weight of the distillate and stirring the resulting mixture for 2 to 3 hours.

Then the alkali-treated mixture is allowed to stand still to be separated into an aqueous phase and an organic phase. After removing the aqueous phase, the remaining organic phase is further washed with water and dried over, for example, sodium sulfate or magnesium sulfate. Thus, modified basil essential oil is obtained.

The modified basil essential oil thus obtained is in the form of an amber liquid containing 87% by weight or more of sesquiterpene compounds and has a good odor or scent.

EXAMPLE

Example 1

1,000 g of natural basil essential oil was distilled by using a 10-plate rectifying tower. During the distillation, the pressure was maintained at a reduced level (3.0 mmHg). 900 g of fractions ranging from the first run to the fraction of a boiling point of 82° C. were removed and 50 g of a fraction of a boiling point of from 83° to 92° C. was distilled. To 50 g of the distillate was added 50 ml of a 1 N aqueous solution of NaOH followed by stirring for 2 hours. The obtained mixture was transferred into a separatory funnel and allowed to stand for 0.5 hour. After removing the aqueous phase, the organic phase was further washed with 50 ml of water and dried over sodium sulfate.

Thus 49 g of an amber oil having the following composition (% by weight of the modified basil essential oil) was obtained. This oil ( the invention product 1) had an odor wherein greenness, freshness and herbiness were highly accentuated.

For comparison, the composition (% by weight) of basil essential oil (comparative product 1) obtained by conventional steam distillation is also given.

| Composition | Invention product 1 | Comparative product 1 |
|---|---|---|
| sesquiterpene hydrocarbons | 90% | 10% |
| oxygenated sesquiterpenes | 5% | 0.3% |
| estragole | 0.03% | 65% |
| linalool | 0.001% | 15% |
| eugenol | 0.03% | 5% |

To illustrate the effects of the present invention, the following Test Example will be given.

TEST EXAMPLE

The invention product 1 and the comparative product 1 were organoleptically evaluated by the following method. The results are as follows.

Organoleptic evaluation 10 parts by weight of each of the invention product 1 and comparative product 1 was separately added to 990 parts by weight of a perfume composition for shampoo as shown below. Each mixture thus obtained was organoleptically evaluated in a pair test by 20 experienced panelists.

The perfume composition as given below was a common compound perfume for cosmetics having a note wherein a floral note of jasmine or rose was a base note and a green note was a top note.

| Perfume composition for shampoo: | parts by weight |
|---|---|
| 1. Orange Guinea | 100 |
| 2. Ligustral[1)] | 4 |
| 3. rose base[2)] | 200 |
| 4. jasmine base[3)] | 240 |
| 5. methyl dihydrojasmonate | 50 |
| 6. Sandalwood Mysore | 30 |
| 7. methylionone alpha | 20 |
| 8. musk ketone | 30 |
| 9. coumarin | 25 |
| 10. diethyl phthalate | 291 |
| Total | 990 |

Note
1)a specialty chemical of Quest Co.
2) and 3)A compound base prepared by Kao Corp.

Results

Among the 20 panelists, 19 evaluated that the mixture containing the invention product 1 was more accentuated in the attributes of herbiness and naturalness.

What is claimed is:

1. A modified basil essential oil containing 87% by weight or more of sesquiterpene compounds, wherein said sesquiterpene compounds comprise sesquiterpene hydrocarbons and oxygenated sesquiterpenes, and wherein said sesquiterpene hydrocarbons are present in an amount of 85% by weight or more, and said oxygenated sesquiterpenes are present in an amount of 2% by weight or more.

2. A modified basil essential oil as claimed in claim 1, wherein the content of each of estragole, linalool and eugenol is 0.5% by weight or less.

3. A process for producing a modified basil essential oil which comprises rectifying basil essential oil to thereby distill a fraction of a boiling point of from 82° to 92° C. under reduced pressure, treating the distillate with an aqueous alkali and removing the aqueous phase to thereby give the modified basil essential oil as claimed in claim 1.

4. A process for producing a modified basil essential oil as claimed in claim 3, wherein the alkali treatment of the distillate is effected by mixing the distillate with an aqueous solution of an alkali under stirring.

5. A modified basil essential oil produces by a process comprising:

a) rectifying basil essential oil to obtain a distillate fraction having a boiling point of from 82° to 92° C.;

b) treating said distillate fraction with an aqueous alkali to obtain an aqueous phase and an organic phase; and c) removing said aqueous phase and obtaining said modified basil essential oil from said organic phase.

6. The modified basil essential oil according to claim 5, wherein said rectifying step (a) is performed under reduced pressure and at a temperature of from room temperature to 120° C.

7. The modified basil essential oil according to claim 6, wherein said rectifying step (a) is performed at a pressure of from 2.0 to 3.0 mm Hg.

8. The modified basil essential oil according to claim 5, wherein said rectifying step (a) is carried out in a rectifying tower having 10 or more plates.

9. The modified basil essential oil according to claim 5, wherein said treating step (b) comprises mixing said distillate fraction with an aqueous alkali solution while stirring, and allowing the resulting mixture to stand until separated into said aqueous and said organic phase.

10. The modified basil oil according to claim 9, wherein said mixing comprises adding 90 to 110 parts by weight of a 0.8 to 1.2 N aqueous solution of an alkali selected from the group consisting of sodium hydroxide, sodium carbonate, potassium hydroxide, and calcium hydroxide, to 100 parts by weight of distillate, and stirring the resulting mixture for 2-3 hours.

11. The modified basil essential oil according to claim 5, wherein said obtaining said modified basil essential oil comprises washing said organic phase with water and drying the resulting washed organic phase over sodium sulfate or magnesium sulfate, to obtain said modified basil essential oil.

12. A modified basil essential oil produced by a process comprising:

a) rectifying basil essential oil at a temperature of from room temperature to 120° C. and at a pressure of 2.0 to 3.0 mm Hg to obtain a distillate fraction having a boiling point of from 82° to 92° C.;

b) mixing 100 parts by weight of said distillate fraction with 90 to 110 parts by weight of a 0.8 to 1.2 N aqueous solution of an alkali selected from the group consisting of sodium hydroxide, sodium carbonate, potassium hydroxide, and calcium hydroxide, stirring the resulting mixture for 2-3 hours, and allowing the resulting mixture to stand until separated into an aqueous phase and an organic phase;

c) removing said aqueous phase, washing said organic phase with water and drying the washed organic phase over sodium sulfate or magnesium sulfate, to obtain said modified basil essential oil.

13. The process for producing a modified basil essential oil of claim 3 wherein said rectifying is carried out at a pressure of from 2.0 to 3.0 mm Hg.

* * * * *